United States Patent [19]

Servos

[11] 4,023,561
[45] May 17, 1977

[54] WATER CALORIC SYSTEMS AND METHODS FOR INDUCING NYSTAGMUS

[76] Inventor: Gerald H. Servos, 21 W. Crescent Blvd., Glen Ellyn, Ill. 60137

[22] Filed: Apr. 18, 1975

[21] Appl. No.: 569,442

[52] U.S. Cl. .................... 128/2.1 R; 128/2.1 M
[51] Int. Cl.² ................................ A61B 5/10
[58] Field of Search ........ 128/2 R, 2 T, 2 Z, 2.1 M, 128/2.1 R, 225; 222/146 HE; 401/188

[56] References Cited

UNITED STATES PATENTS

| | | | |
|---|---|---|---|
| 1,522,601 | 1/1925 | Strobel | 128/225 |
| 2,589,728 | 3/1952 | Pratt | 128/225 |
| 2,709,542 | 5/1955 | Eller et al. | 401/188 X |
| 3,239,649 | 3/1966 | Reeve | 222/146 HE |
| 3,563,231 | 2/1971 | Ducote et al. | 128/2.1 R |
| 3,676,010 | 7/1972 | Kirch | 401/188 |
| 3,794,017 | 2/1974 | Servos | 128/2.1 M |

*Primary Examiner*—William H. Grieb
*Attorney, Agent, or Firm*—Alter and Weiss

[57] ABSTRACT

Systems and methods for delivering waters at different temperatures to the patient's ears to induce nystagmus. The systems use compressed air to deliver water at a specified temperature to the selected ear of the patient. The system vis-a-vis pump systems is quieter, thermally more efficient and diagnostically improves the entire nystagmus process.

2 Claims, 5 Drawing Figures

WATER CALORIC SYSTEMS AND METHODS FOR INDUCING NYSTAGMUS

This invention relates to systems and methods used for measuring nystagmus responses in the vestibular systems; and ;more particularly, to the systems and methods used in inducing nystagmus when the temperature of the patient's middle ear is changed to induce the nystagmus condition.

It has been found that under conditions of nystagmus, the eyeball moves relatively slowly to the right or to the left, and then moves at a higher velocity towards the starting eyeball positon. That is, the eyeball oscillates under induced nystagmus conditions moving to the right or left side of the eye cavity in the cranium. When the eyeball reaches the limit of such movement, it moves back toward the starting position at a relatively high rate of speed. A similar vertical component exists in the movement of the eyeball under induced nystagmus.

The most common method of inducing nystagmus is to preheat water in a tank, pump the water through a delivery tube into the ear of the patient. The system is relatively noisy, because of the pump noise, Furthermore, since the water goes through a water pump, it tends to pick up heat and dirt normally generated by water pumps. Also, heat is added during the pumping process.

Accordingly, an object of the present invention is to provide new and unique systems and methods for delivering pre-heated water to the patient's ears to induce nystagmus.

A related object of the present invention is to use air pressure that is available in many physician's offices to force pre-heated water through a delivery tube into the ear of the patient.

Yet another object of the present invention is to provide systems for delivering pre-heated water to the ear of the patient without the direct use of water pumps.

Another related object of the present invention is to provide systems and methods for delivering pre-heated water to the patient's ear for inducing nystagmus, wherein a pair of transparent enclosures are provided. The heat is generated in the water by electrical heaters. The transparent enclosures enable monitoring the sufficiency of the heated water supply.

Yet another object of the present invention is to provide complete systems for delivering pre-heated water to the ears of patients for inducing nystagmus, wherein the water temperature of the water supply in reservoirs is thermostatically controlled and means are provided for continuously circulating water in the reservoirs to obtain a relatively constant temperature over the water in the reservoir.

Yet another object of the present invention is to provide methods of inducing nystagmus using pre-heated water wherein no pumps are directly utilized.

In accordance with one embodiment of the invention, a pair of air tight containers are provided as a water supply source. Air pressure is delivered to both containers. A simple clamp type valve prevents water from flowing out of the delivery tips. Opening that valve causes the pre-heated water therein to pass through a delivery tube to the ear of the patient for inducing nystagmus.

Means are provided for continuously monitoring the sufficiency of the pre-heated water supply in the tank, and means are further provided for maintaining the desired temperature of the water and for assuring that the temperature of the water is constant throughout the container. The above mentioned and other objects and features of this invention together with the manner of obtaining them will become more apparent and the invention itself will be best understood by making reference to the following description of a preferred embodiment of the invention taken in conjunction with the accompanying drawings, wherein:

Figure 1:
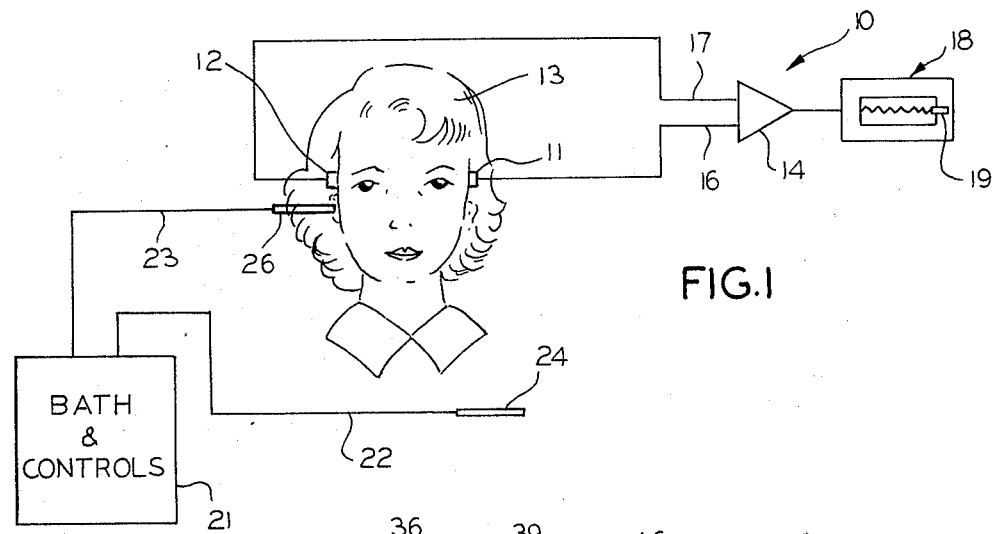
FIG. 1 shows in block diagram form a system inducing nystagmus, and recording the eyeball movement during the induced nystagmus.
Figure 5:
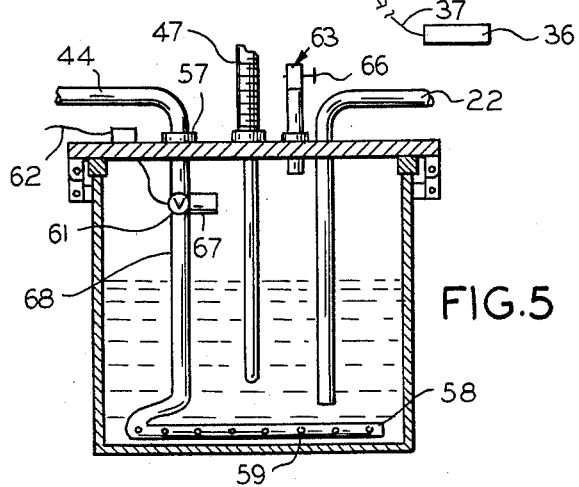

FIG. 5 shows an air bubbler system for assuring continuous circulation of the liquid in the container for maintaining a constant temperature of the liquid. Turning now to the drawings, FIG. 1 shows in block diagram form, apparatus generally designated as 10 for recording the position of the eyeball under induced nystagmus as a function of time. More particularly, means are provided for sensing the cornea retina potential differences at the patient's temple. The potential difference is used to control a recorder. For example, electrodes 11 and 12 are fastened by means, such as an adhesive tape, to the temples of the patient indicated at 13.

The example is given showing electrodes 11 and 12 for detecting the cornea retina potential differences caused by horizontal movement. Electrodes can also be fastened above and below the eye to measure the vertical movement of the eyeball under conditions of induced nystagmus. The operation of the invention would be as effective under such conditions as they are for the horizontal measurements described hereinafter.

The output signals of each of the electrodes 11 and 12 are coupled to a high gain amplifier 14 through leads 16 and 17, respectively. The amplifier output of the high gain amplifier is coupled to drive a recording oscillograph shown generally as 18. Responsive to the receipt of the amplified signal from the amplifier 14, a pen 19 of the oscillograph is driven from a central zero location, either upwardly or downwardly, providing a trace continuously showing the position of the eyeball as a function of time. When the eyeball is positioned so that the patient is looking directly forward, the pen should be in the zero position. Any movement of the eyes to the right or to the left produces a cornea-retinal potential, that is a function of the distance the eye moves from the zero position.

The nystagmus condition is stimulated by causing a temperature differential between the body and labrynth of the right and left ears. The temperature differential used for the caloric stimulation is obtained by flooding a selected ear canal with water at a desired temperature. Each ear is stimulated with water at a temperature, either 7° C above the body temperature or 7° C below the normal body temperature, for 30 seconds. Water that is at a temperature which is 7° C above the body temperature is commonly referred to as the hot temperature, and the water which is 7° C below the body temperature is commonly referred to as the cold temperature. Standard temperatures of 30° and 44° C are normally used.

The apparatus and methods described hereinafter are for eliciting the nystagmus condition by delivering fluid, such as water at desired temperatures to the ears of the patient. More particularly, means, such as the container or tank and controls generally shown at 21, are provided for heating and storing the water to be used. Extending from the tank and controls 21 are delivery tubes 22 and 23 for delivering the water to the left and right ears of the patient.

Figure 2:
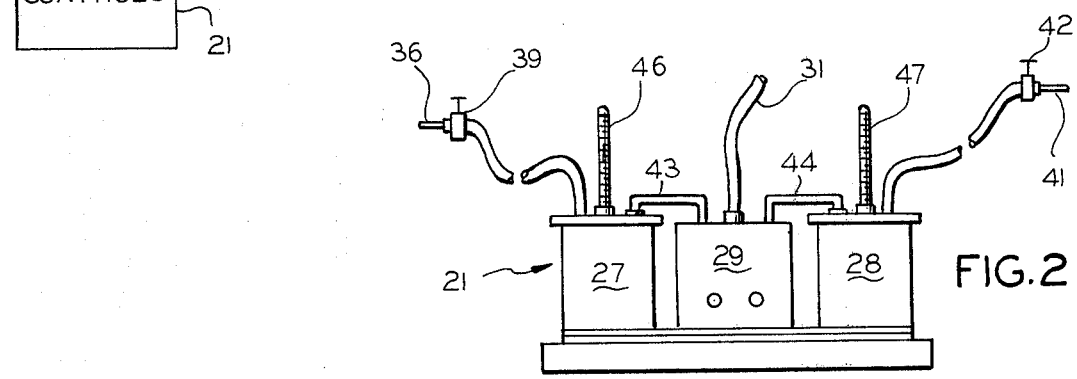
FIG. 2 is a front view of the heated water containers, used in delivering the water from the container to the ears of the patient, and the air pressure supply controls.

Means are provided for moving the water through the delivery tubes into the selected ear of the patient through delivery heads 24 and 26 attached to tubes 22 and 23, respectively. In the presently available apparatus the water is forced from the bath to flush the ear using pumping means. The bath and controls 21 do not use any pumps. Instead, as shown at FIG. 2, pressurized containers are provided. In greater detal, FIG. 2 shows a pair of pressurized containers 27 and 28, attached to a pressure regulator station 29. High pressure air is brought into regulator station 29 through pressure tubing 31.

Figure 3:
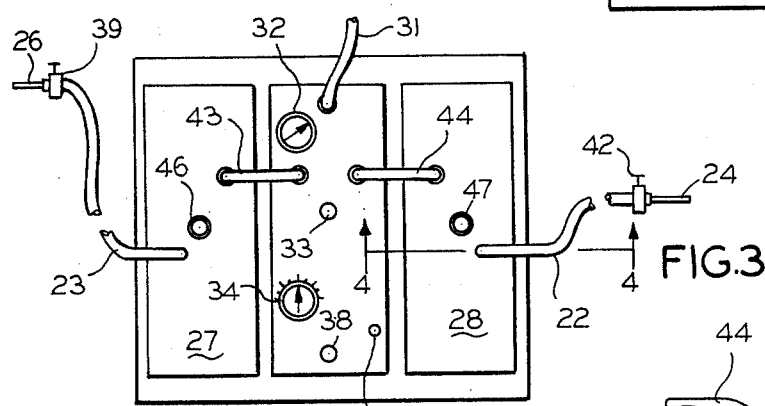
FIG. 3 is a plan view of the containers and controls shown in FIG. 2.

The regulator station, as shown in FIG. 3, receives the pressurized air delivered through hose or conduit 31. Pressurized air is available in many physicians' offices. Instruments, such as air pressure indicator 32 for monitoring the air pressure at hose 31, are provided in the regulated air pressure station 29. An air pressure adjustment control 33 is provided. Timing means 34 is also provided limiting the time period during which the heated water is delivered to the ear of the patient.

Means are provided for starting the timer 34. More particularly, as shown herein, a foot switch 36 is actuated by the operator of the nystagmus inducing equipment to start the timer. The foot switch 36 is coupled to the pressure regulator compartment and controls through conductor 37. The timer in one embodiment sounds an audible signal which alerts the operator to remove the delivery head from the subject's ear.

The heater switch 38 is operated to the "on" position to bring the water in the containers up to the desired temperature. When the water is at the desired temperature, the delivery heads 24 or 26 are alternately placed in opposite ears and the appropriate clamp 39 or 42 is loosened. Simultaneously, the timer is started. The operator or doctor keeps the clamp open until the timer signals that the irrigation period is over.

The pressurized air coming in through tube 31 goes through a regulator (not shown) in the regulator portion and from there through tubes 43 and 44 to baths 27 and 28, respectively. Each of the baths is shown as having a thermometer therein. For example, bath 27 is shown as having thermometer 46 therein; while bath 28 has thermometer 47 therein. This enables a constant check of the water temperature.

Figure 4:
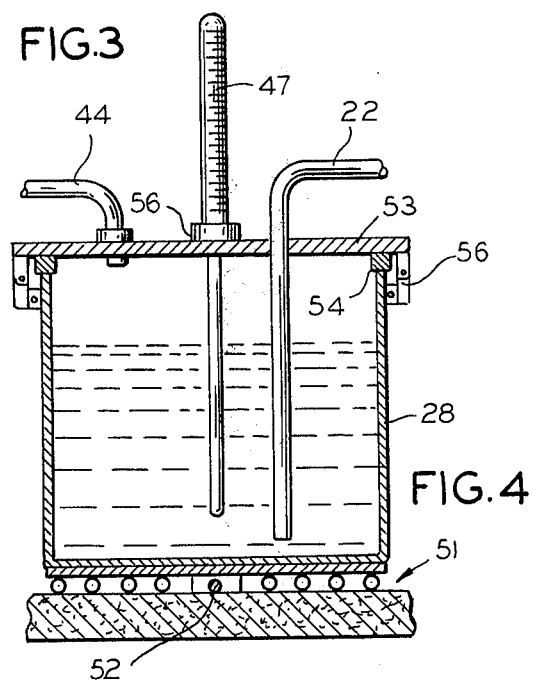
FIG. 4 is a sectional view of one of the containers.

As best seen in FIG. 4, the temperature of the water is raised using means, such as heating element 51, controlled by thermostatic means, that is shown having an adjustment screw 52. Immersion type heating elements and thermostatic means can, of course, be used within the scope of the invention. The baths themselves preferrably comprise glass tanks which are covered by a metal cover 53. The glass tanks are transparent to thereby enable a constant check on the amount of fluid in the tank 28.

Means are provided for sealing the bath vessel. More particularly, a soft rubber or plastic gasket 54 is located at the top of the vessel and the cover 53 fits thereon. The cover 53 is held in place by spring clasps, such as clasp 56 of the type normally used on luggage, for example. The clasps hold the cover 53 tightly in place on top of the gasket 54.

Means are further provided for enabling the thermometer to pass through the cover 53 with a minimum of air leakage. More particularly, grommets are provided around the aperture utilized by the thermometer and by the air pressure tubes. For example, grommet 56 is shown at the aperture through which the air pressure supply tube 44 passes. It should be noted that while grommets and latches are shown, any other means of sealing the tank is within the scope of this invention.

FIG. 5 shows another and further embodiment of the invention wherein means are provided for assuring that the air in the bath circulates to thereby maintain an equalized temperature throughout the liquid in the bath. Thus, hot water is circulated through means other than the normal consection caused by the heating coils, such as heating coil 51, at the bottom of the bath. More particularly, the air line 44 is shown as leading to the bottom of the water and having an apertured portion 58, having apertures, such as aperture 59 therein. Bubbles of high pressure air escape from the apertures and agitate the water to materially increase the circulation of the water. The increased circulation ensures that there is equalized temperature throughout the water.

A further refinement of the bubbler systems shown in FIG. 5 is the valve 61 operated by switch 62. The valve selectively directs the air to either go through the bubbler arrangement 68 or directly into the top of the pressurized container. Thus, the same air is conveniently used for increasing the circulation and for forcing the water in the patient's ear.

While the principles of the invention have been described above the in connection with specific apparatus and applications it is to be understood that this description is made only by way of example, and not as a limitation on the scope of the invention.

I claim:
1. A liquid caloric system for inducing nystagmus in patients,
said system comprising bath means for storing liquids to be delivered to the patient's ear for inducing nystagmus, patients,
said bath means comprising a pair of air tight liquid containers,
air pressure means for forcing the liquid from each of the containers,
said air pressure means comprising a control section common to both of said containers,
means for coupling said common control section to external sources of compressed air commonly available in physicians offices,
said common control section comprising air pressure control means for controlling the actual air pressure delivered to said container,
means for heating the liquid in at least one of said containers,
said means for heating the liquid including means for monitoring and controlling the temperature of the liquid, air tube means separately coupling air under pressure from said common control section to each of said containers, said air tube means comprising at least one tube extending to and along the bottom of said at least one container, said one tube having perforations therein to enable air under pressure to escape from the tube to agitate the liquid and assure equal temperature throughout the heated bath, air tube valve means in said air tube means to cause air to selectively flow to the extension along the bottom of said container or to exit the one tube at the top of the liquid, and delivery tubes attached to each of the containers for delivering the liquids to the ears of patients at controlled rates regardless of the position of the delivery tubes relative to the height of the containers.

2. The liquid caloric system of claim 1 wherein said air pressure control means includes means for regulating the pressure of the air, means for monitoring the regulated pressure, and first valve means for controlling the flow of water under pressure to selectively stop the flow or enable the flow of water from the bath means to the patient's ear.

* * * * *

UNITED STATES PATENT OFFICE
CERTIFICATE OF CORRECTION

Patent No. 4,023,561          Dated May 17, 1977

Inventor(s) Gerald H. Servos

It is certified that error appears in the above-identified patent and that said Letters Patent are hereby corrected as shown below:

Col. 3, line 20    -    After the words "In greater", the word "detal" should be --detail--.

Col. 4, line 24    -    After the word "normal" the word "consection" should read --convection--.

Col. 4, line 41    -    After the word "above" delete "the".

Col. 4, line 51    -    After the word "nystagmus", delete the word "patients".

Col. 4, line 52    -    the following sentence is omitted:

--means for measuring the nystagmus response of the patients --.

Signed and Sealed this

Twenty-seventh Day of September 1977

[SEAL]

Attest:

RUTH C. MASON          LUTRELLE F. PARKER
*Attesting Officer*     *Acting Commissioner of Patents and Trademarks*